Figure 1:
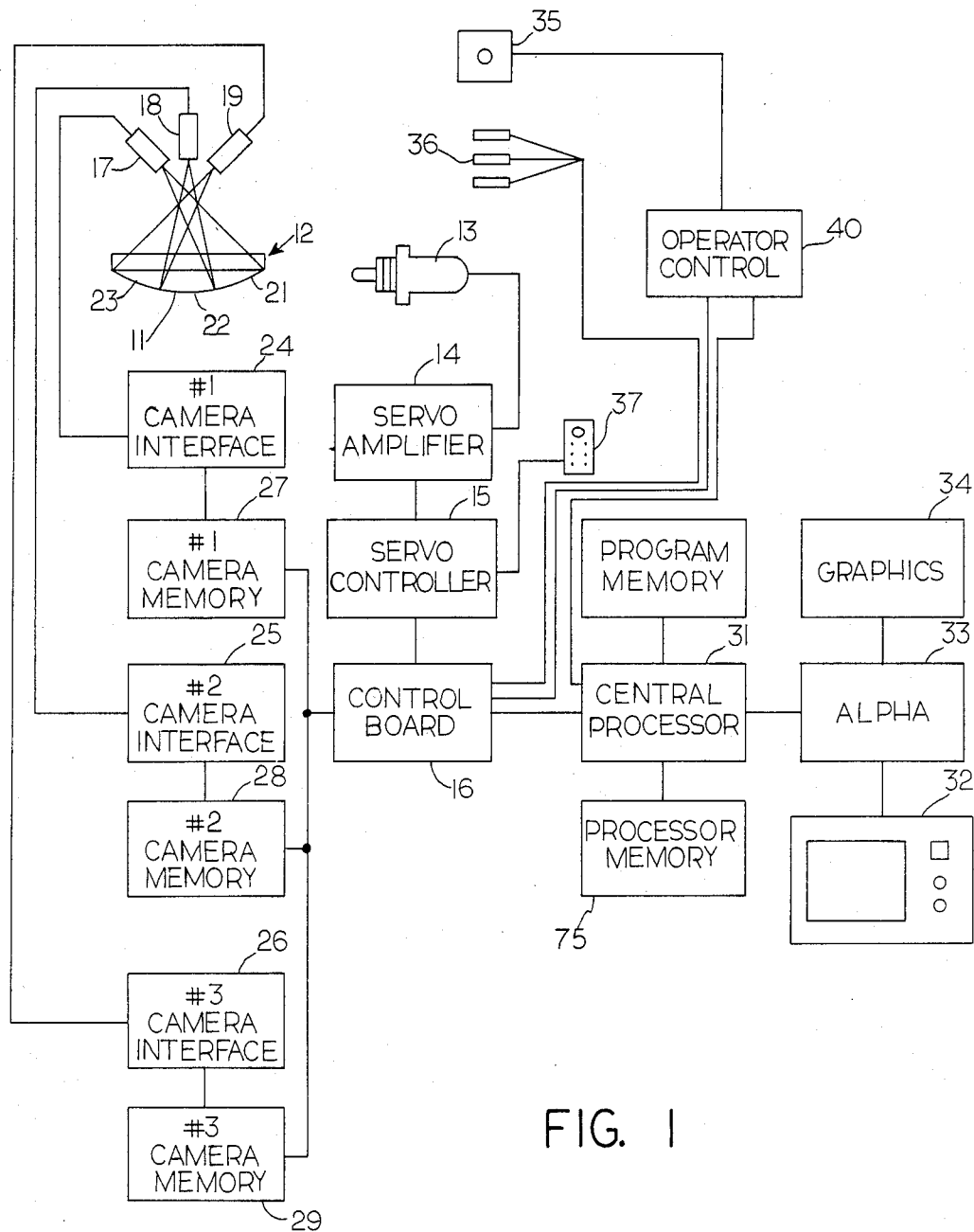

United States Patent [19]

Miller

[11] Patent Number: 4,820,932

[45] Date of Patent: Apr. 11, 1989

[54] METHOD OF AND APPARATUS FOR ELECTROOPTICAL INSPECTION OF ARTICLES

[75] Inventor: John W. V. Miller, Toledo, Ohio

[73] Assignee: Owens-Illinois Television Products Inc., Toledo, Ohio

[21] Appl. No.: 58,207

[22] Filed: Jun. 4, 1987

[51] Int. Cl.$^4$ .......................................... G01N 21/88
[52] U.S. Cl. ................................. 250/563; 250/562; 358/106
[58] Field of Search ................... 250/223 B, 562, 563, 250/572; 356/240; 358/106; 209/526

[56] References Cited

U.S. PATENT DOCUMENTS

| | | | |
|---|---|---|---|
| 4,002,823 | 1/1977 | Van Oosterhout | 250/223 B X |
| 4,378,494 | 3/1983 | Miller | 356/240 |
| 4,380,025 | 4/1983 | Deane | 358/106 |
| 4,403,294 | 9/1983 | Hamada et al. | 250/562 X |
| 4,428,672 | 1/1984 | Allard et al. | 250/563 X |
| 4,642,813 | 2/1987 | Wilder | 358/106 X |

FOREIGN PATENT DOCUMENTS 3314465 10/1984 Fed. Rep. of Germany ...... 250/563

Primary Examiner—David C. Nelms

[57] ABSTRACT

A system for line scan processing video signals from a linear array of photoelectric cells so that the signals for individual cells and individual scan sweep are selectively utilized according to sweep number and cell numbers. A signal window is defined for each sweep individually at a predetermined cell for a beginning of the effective video signal and is terminated at another predetermined cell for the end of the effective video signal so that the video signal is processed for only that portion of each sweep covering the area of interest. In optical inspection of an article the significance of changes in the ratio of light intensity at particular cells from the background light intensity is adjusted by sweep and cell number so that such changes which are predictable in certain locations on the article must exceed threshold levels which are different than for other locations. This enables compensation in the inspection of a number of similar articles for regularly occurring marks on the areas of inspection for those articles.

29 Claims, 2 Drawing Sheets

METHOD OF AND APPARATUS FOR ELECTROOPTICAL INSPECTION OF ARTICLES

The present invention relates to electrooptical inspection methods and apparatus and in particular to the interface logic and circuitry for a line scan of data collected during such inspection.

The use of optical scanning devices for inspection of articles is well known. Systems such as those shown in U.S. Pat. Nos. 3,708,680 and 3,716,136, have circuitry including means for receiving and interpreting light passed through or directed onto an item subject to inspection. Such devices incorporate either a visual display for comparison of the item or employ a means capable of producing an electrical signal proportional to the intensity of light passing through, scattered from, refracted from, or reflected from the item. The output of these devices is compared against a standard to determine if the item under inspection is suitable as to size and construction and is without unacceptable defects.

U.S. Pat. No. 3,877,821 discloses an apparatus having a scanning array of photosensitive devices that receives light from discrete areas of the item under inspection and is serially interrogated to generate a train of pulses having amplitudes representing the light received from the item. Adjacent pulses are compared to generate signals having amplitudes which represent the difference in pulse amplitudes. The different signals can be utilized to indicate a defect in the object being inspected. U.S. Pat. No. 3,942,001 discloses an apparatus for detecting the presence of extraneous matter or cracks in translucent containers. A beam of light is projected through the container to generate an inspection signal which is compared with an acceptance signal. The acceptance signal amplitude is varied in accordance with the position of the spot beam with respect to the container.

Glass bottles have been inspected ufilizing data signals generated from a line scan camera having an aligned array of photodiodes, an optical system including a light source for directing light to a bottle and thence to the line scan camera, and means to advance bottles individually into the optical system and rotate them while in that system. A multiplicity of scans of the bottle at different rotational positions in the optical system enable all or a portion of the bottle sidewall to be inspected. Event signals, indicative of defects or inclusions, are generated when the magnitudes of adjacent photodiode signals differ by an amount which exceeds a threshold level. Signals are also generated to identify the location of each event signal with respect to a corresponding photodiode and to identify the scan of the object in which the event signal was generated to associate the event signal with a location on the object, U.S. Pat. Nos. 4,378,494, 4,378,495, 4,432,013, 4,437,116 and 4,467,350 disclose such systems with adjuncts such as processing means for event signals to identify and evaluate adjacent defects in the same and/or adjacent scans and compare such processed signals with predetermined values to identify defects, means to display the event signals as a two-dimensional representation of the surface of the bottle as if it has been cut and unwrapped, means to set threshold values to optimize defect detection performance, paired control units alternately to process inspection data and thereby speed the inspection process with one unit processing data while the other unit receives data, and signal comparison means for minimizing general light variations across the object.

Large objects which are transparent, such as the viewing faces of cathode ray tube faceplates, can be inspected employing line scan techniques. In U.S. Pat. No. 4,606,634 there is disclosed an arrangement for translating the viewing face of a faceplate through an optical system including a source of illumination on one side and means to pass light through the viewing area to a plurality of line scan cameras having their aligned photodiode arrays aligned. In the case of faceplate viewing surfaces, optical quality requirements dictate high resolution inspection. For example, three cameras each with one thousand twenty four aligned photodiodes are disclosed in 4,606,634, to span the minor dimension of a rectangular faceplate.

The processing of faceplates for cathode ray tubes (CRT) involves a number of steps in which there is substantial value added subsequent to the forming and annealing of the raw glass. High optical quality is required for the viewing area of CRT faceplates since defects, particularly buried defects such as blisters and stones, of relatively small size become quite apparent and objectionable in the finished viewing screen. Visual inspection is made of faceplates at several points in their processing beginning with their delivery from the annealing lehr following their formation.

Faceplates are coded and marked early in their processing as at the time the studs for mounting shadow masks are inserted in the faceplate flange. Such marks may be on portions of the viewing surface. Additional marks may be developed by contact with the lehr mat as the faceplates are conveyed through the annealing lehr. Certain superficial markings can be disregarded in the initial inspections including code markings and lehr mat marks, since they are removed in subsequent grinding, polishing and cleaning steps.

Heretofore electrooptical inspection of CRT faceplates has not been utilized in the early phases of processing in part, because the inspection could not accommodate and distinguish those defects which were detected and could be diregarded from those which were cause for rejection or lower quality categorization.

The present invention is arranged with logic to develop arbitrary inspection windows and inspection acceptance thresholds employing line scan camera techniques of inspection. In such techniques a linear array of photodiodes arranged to respond to light intensity from discrete areas of a surface being inspected is scanned to respond to optical defects resulting in light of intensity representative of the defects in the discrete areas. A repetition of line scans of adjacent lines of areas across the viewing face of the faceplate affords an inspection of the entire faceplate. In order to accommodate the predictably located acceptable blemishes, the inspection windows and threshold levels are set during scans to accommodate those blemishes of the areas in which the blemishes are anticipated as a function of diode and sweep number. Camera diode start and stop limits are set for each scan thereby inhibiting response to areas outside those to be inspected, as along the edges of the faceplate viewing region where the faceplate flange is present and where the flange merges into the viewing region. Different regions of the area enabled for inspection can be set at different thresholds of light intensity to accommodate the regularly experienced marks on the viewing region which can be tolerated since they can be removed later.

The camera scan of its diode array is clocked and a counter generates diode addresses. At the end of each scan the diode counter is reset and the sweep number is advanced to provide a sweep address to a counter which was reset at the beginning of an inspection sequence.

The signals from diodes subject to scan interrogation which are of a threshold level are classified as "events" and actuate an event counter and event address. The addresses drive memories to store events as to location and magnitude for processing in a central processing unit which is programmed to accept, reject, or grade the article under inspection and collects data as to the nature of defects represented by the detected events, the location, the size of such defects, their density as to region of the viewing area and the like.

Figure 2:
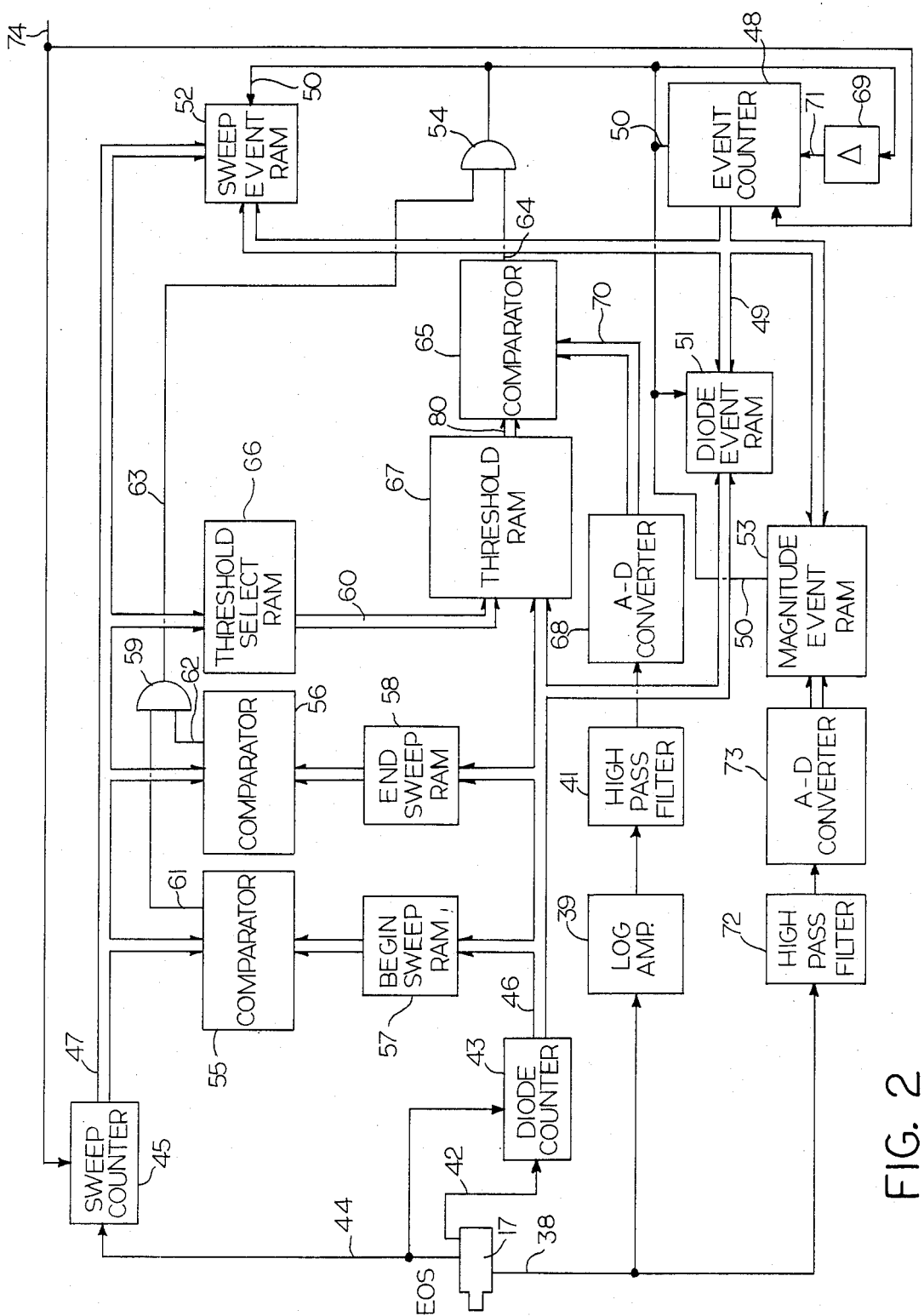

The above and additional features of this invention will be appreciated more fully from the following detailed description when read with reference to the accompanying drawing in which:

FIG. 1 is a block diagram of a system according to this invention for inspecting CRT faceplates; and FIG. 2 is a block diagram of the camera interface and memory circuitry of FIG. 1 in which logic functions according to this invention are performed.

A typical system employing the method and apparatus of this invention is shown in FIG. 1 in conjunction with an electrooptical faceplate inspection system for detecting stones and blisters in the viewing region 11 of a flanged faceplate 12. Faceplate 12 is mounted on a cradle and in an optical system (not shown) as illustrated in U.S. Pat. No. 4,606,634 the disclosures of which are incorporated herein by reference, which rocks it into and out of the paper, as viewed in FIG. 1, under the control of a servo motor 13 driven by a servo amplifier 14 from a servo controller 15. Servo controller is coordinated with inspection camera operations from a control board 16 so that scans of transverse bands of the viewing region 11 are made as the bands are positioned in the optical path to the cameras by the servo drive of the cradle. Typically a twenty-five inch rectangular faceplate (diagonal dimension) has a fifteen inch width and a twenty inch length and the system of cameras 17, 18 and 19 is arranged with three linear arrays of diodes each comprising two thousand forty-eight diodes which when aligned with a slight overlap provides six thousand pixels each of which corresponds to discrete viewed areas of the faceplate for each scan along the aligned array of fifteen inches of the minor dimension of the viewing region 11. The major dimension of viewing region 11 is scanned in eight thousand scans as the faceplate is traversed through the band field of view of the cameras.

The number 1, 2 and 3 cameras 17, 18 and 19 are shown focused at regions 21, 22 and 23 respectively on the inner surface of faceplate viewing region 11 and a source of uniform light intensity (not shown) is directed on the outer surface of region 11 from below as viewed in FIG. 1. Each camera has an aligned array of photodiodes (not shown) which issue electrical signals as a function of the light intensity they receive from their respective discrete areas in region 21, 22 or 23 as the case may be and thus as a function of the degree of transparency of these points or areas in an optical system that selectively excludes refracted light as described in U.S. Pat. No. 4,606,634.

The analog signal representing light at each discrete area is scanned in each camera as the diode array is scanned under control of a camera clock which can be on control board 16 and is processed for the system in individual camera interface circuits 24, 25 and 26 which ascertain those signals representing reduced pixel illumination as to threshold levels, diode and scan number. Only those signals which may be indicative of a defect are recognized and designated "events" for the remainder of the processing functions of the system.

The magnitude, diode number and scan number of events are stored in respective camera memories 27, 28 and 29 and are accessed through control board 16 by the central processor 31 to develop inspection information. The central processor can issue grade classifications for the faceplates based upon the number of events, the location of the events and the magnitude of the events and any combination of these factors. The exemplary system has a resolution capacity of about 3 mils and thus will detect defects which are essentially invisible to the human eye. Further, it will detect longer defects represented as a string of events which may or may not be significant to the utility of a display tube produce from the faceplate.

Inspection system outputs can include a display of the viewing region 11 with the defects portrayed as to location, size and shape on a monitor 32, as data in alphanumeric form and graphically as developed by control circuits 33 and 34 coupled between the central processor 31 and monitor 32.

Additional adjuncts of the system can include control switches, represented by start button 35, cradle limit switches 36, servo manual control 37, reset buttons, keyboards to set parameters, call up program menus and the like, many of which are not shown and are represented by operator control 40.

A block diagram of a camera interface and a camera memory block of FIG. 1 is shown in FIG. 2 wherein inputs from the camera 17 and its controls include the analog signal input 38 which supplies signals from the currently scanned camera diode to logarithmic amplifier 39 and high pass filter 41, camera clock input 42 to diode counter 43 and end of sweep input 44 to sweep counter 45. Camera clock input 42 applies pulses corresponding to the scan steps for scanning the linear array of diodes in the camera and this results in an advancing pulse to the diode counter 43 which places that counter at the pixel or diode number of the currently scanned diode and thus the area number on faceplate 11 surface region 21 subject to inspection. The diode counter 43 is reset at the end of each sweep of the diode array by a signal from the end of sweep input 44 so that its count starts from its reset value for each scan and it issues on "Diode Number" bus 46 the digital number designating the diode currently scanned. That end of sweep signal is derived from the camera scan control at the end of each diode array sweep to add a count to sweep counter 45 identifying the next scan number on "Sweep Number" bus 47. A reset of sweep counter 45 is issued at the end of each inspection routine by the central processor 31.

The significant data to be created in the system in the occurrence of events or sensed optical changes indicative of defects or blemishes. Event RAM address data is derived from event counter 48 over "Event RAM Address" bus 49 to cause the event memories to store the diode number of the event in "Diode Event" RAM 51, the sweep number of the event in "Sweep Event" RAM 52 and the magnitude of the event in "Magnitude Event" RAM 53. These event circuits are enabled through "Event Enable" AND 54 in response to a signal from the currently scanned diode of a magnitude equal to or greater than the predetermined threshold signal magnitude for that diode during that scan, provided the signal is derived from a diode within the predetermined window for that sweep.

The window of acceptance of diode signals as events is defined by sweep and diode numbers for the beginning and end of each sweep by "Begin Window" comparator 55 and "End Window" comparator 56. The effective sweep number is supplied in digital form on bus 47 to each of the comparators 55 and 56. The currently scanned diode number on bus 46 is supplied to "Begin Sweep" RAM 57 and "End Sweep" RAM 58. A predetermined, individual sweep number to begin the sweep window is set for each diode in RAM 57 and a predetermined, individual sweep number to end the sweep window is set for each diode in RAM 58. Each RAMs 57 and 58 are arranged to issue digital sweep numbers to their respective comparators 55 and 56 for each digital diode number from "Diode Number" bus 46. When the sweep number on bus 47 from "Sweep Counter" 45 is equal to or exceeds the sweep number in the RAM 57 at the diode count address, comparator 55 issues a "true" enable signal on lead 61 to a coincidence gate requiring "true" signals on both of its inputs to issue an enable signal for the issuance of an event signal. The "Window Defining" AND 59, if enabled by a "true" state on lead 62, is gated through lead 63 to "Enable Event" AND 54. Comparator 56 issues a "true" signal on 62 until the diode address of the sweep applied to "End Sweep" RAM 58 issues the sweep number digital signal to "End Sweep" comparator 56 causing it to remove the "true" state on lead 62. When lead 62 goes "false" as a result of a sweep count from RAM 58 at or above the sweep count on bus 47, AND 59 is inhibited to inhibit AND 54.

Coincidence of enabling signals on leads 63 and 64 gates AND 54 to trigger event counter 48 and issue "Save Event Data" signals on lead 50 to each of the sweep event RAM 52, "Diode Event" RAM 51 and "Magnitude Event" RAM 53. A diode signal meeting the predetermined threshold magnitude results in a signal out of comparator 65.

Each sweep can have threshold levels set for its individual diodes according to the sweep number on bus 47 to "Threshold Select" RAM 66. RAM 66 provides look up tables from which thresholds are set. A convenient arrangement is to provide four available series of threshold levels in "Threshold" RAM 67, one of which is selected via the output 60 of "Threshold Select" RAM 66 for each sweep number. The diode number current subject to scan is applied to "Threshold" RAM 67 from "Diode Number" bus 46 so that the threshold digital signal level for the effective sweep and diode is issued on bus 80 to comparator 65. Analog to digital converter 68 responds the analog signal of the logarithm of the analog magnitude signal from the diode currently subject to scan as issued by logarithmic amplifier 39 which differs from the background illumination level analog signal level developed from prior scanned diodes so as be passed by high pass filter 41 to provide a digital magnitude signal to comparator 65 on "Diode Logarithmic Magnitude" bus 70, as disclosed in greater detail in the cofiled U.S. patent application Ser. No. 058,109 entitled "Method of and Apparatus for Comparing Data Signals in an Electrooptical Inspection System" by the present inventor. If that magnitude is in excess of the threshold digital signal set by "Threshold" RAM 67, comparator 65 will pass an enable signal on lead 64 to "Event Enable" AND 54.

Analog diode signals from camera 17 are passed on lead 38. In order to enhance the extraction of information from the video signal made up of the diode signals on an illumination invariant basis, nonlinear filtering is employed. In U.S. Pat. No. 4,432,013 a subtraction of successive logarithms of digital signal values of analog camera diode signals is employed by passing the camera video through an analog to digital converter, latching the first converted diode signal, ascertaining the logarithm of that digital value, and summing it with the logarithm of the next diode signal digital value. Thus a slowly changing light level variation at the camera results in small logarithmic differences which are not registered as optical defects while abrupt changes are registered as defects. In the present illustrative arrangement, the video signal envelope of the signal levels of a scan of the diodes in the line scan camera is subject to high pass filtering so that it responds directly to the individual pixel analog signal deviations from the weighted average over the group of pixels scanned previously, permitting the use of analog filters and a more direct treatment of the signal as shown and discussed in greater detail in the aforenoted copending U.S. patent application Ser. No. 058,109.

Those abrupt changes in detected light during a scan result in signals which are passed by two channels each including a high pass filter while slow changes are blocked by the filters. The camera analog signals on lead 38 are utilized for absolute magnitude values in "Magnitude Event" RAM 53 by filter 72 and converter 73, and are converted to logarithmic values by logarithmic amplifier 39 which responds to light flux intensity at the pixels as logarithmic values which are relatively constant over the smooth portion of the video. Those gradual changes of signal which would result from gradual changes of light level are not passed by high pass filter 41 and have no effect on the following converter 68 or comparator 65. The abrupt changes of the logarithmic signal as would occur as a darker pixel is scanned are passed by high pass filter 41 to analog to digital converter 68 and transmitted to comparator 65. The logarithmic values employed, when high pass filtered, respond to the degree of change of the video signal and not the absolute value of change due to the conversion yet signal filtering can be analog and thus more readily tailored to the system.

Illumination invariant event detection is achieved by the high pass filtering of the logarithmic signal of scanned pixel illumination intensity. For example, a defect which darkens a pixel so that its diode issues a signal which is fifty percent of the signals of diodes for pixels previously scanned and constituting the background illumination level in that region will produce a logarithmic signal differing from the background signals by a uniform amount for all levels of background illumination. The high pass filter 41 will pass only the portion of the logarithmic signals representing the deviation and of a level which is a function of the deviation without regard to the background signal level.

Regularly experienced patterns of varying light transmission over the faces of workpieces within the limits of the enabled portions of the second array, as defined by the gating of AND 59, are accommodated by adjustment of light sensitivey, the light responsive signal threshold of deviation, for the areas in which those patterns occur. Typical patterns are the markings applied to identify the workpiece, such as mold identification applied to CRT faceplates, and tool marks on the workpiece, such as lehr mat marks which occur in the areas of the faceplate contacted by the lehr mat. These patterns occur on predictable areas of the workpiece and may be of a degree of translucence such that defect changes in translucence remain detectable in the inspection system. Thus, a workpiece identification or a tool mark will be present on the same areas within the area subject to optical inspection from workpiece-to-workpiece and the sweep numbers and diode counts at which light transmission levels are shifted from the levels for defect and mark free areas, the background level, are predictable. Further, the degree of change of light transmission from the background level at those locations is also predictable.

Those marks which will not direct from the ultimate quality of the workpiece can be effectively excluded from the inspection process by establishing threshold signal levels which render the inspection system event signal generating means no-responsive to light transmission changes characteristic of the marks when the system is inspecting the areas in which the mark patterns are predicted. A high pass filtered analog logarithmic signal from logarithmic amplifier 39 and high pass filter 41 is converted to a digital signal in converter 68 and applied to comparator 65 which gates AND 54 if the applied signal is equal to or greater than the threshold level applied to the comparator. Adjustment of threshold levels applied to comparator 65 according to the workpiece area current subject to inspection enables the regularly occurring patterns in the workpiece to be accommodated, either by causing the system to disregard the areas containing those patterns by setting threshold levels above those anticipated under any reasonable condition, or by raising the threshold levels to bar comparator response to the regular patterns while responding to anomalies which would be characteristic of defects within the area of the pattern of markings. Thus, no response would result in an event detection if the threshold were set for one hundred percent or total light elimination from pixels in the pattern area and, in effect, the inspection window of the system would be defined by the effective sweep of each of the individual scans and the blanked portion of the individual scans are defined by the threshold settings for the pattern area between the ends of those sweeps. Alternatively, a setting of an intermediate threshold, for example one slightly above the signal level anticipated for the reduction of light intensity at the pixels in the pattern for the workpiece identification mark or tool mark, would enable a response of an event detection signal in the pattern area where the cumulative effect of the anticipated pattern and a defect in the pixel area produces a signal above the intermediate threshold setting.

It is known that a scanned image of uniform light intensity has fringe effects which diminish outwardly from the maximum intensity at each end. These fringing effects can be eliminated in large measure in a line scan camera where image length along the scan is to be ascertained by clipping the signal at its half magnitude level, counting the diode signal pulses which exceed the half magnitude and scaling the number of such pulses to the length to be ascertained. Capability for such length measurements is afforded out of the high pass filter 72 for the video analog signal. The filtered analog video is converted to a digital signal representing the magnitude of the transition from the video base value due to the abrupt change in light intensity by anode to digital converter 73 and is passed as a digital signal to "Magnitude Event" RAM 53. Again the gradual changes in the video signal magnitude are filtered at 72 and only the abrupt changes are effective in following circuits. In order to enhance high pass filtering as an effective means of extracting event signals from a string of diodes, the camera scan rate for the diodes is maintained constant and the time constant of the filter is long relative to the individual pixel scan intervals as set forth in greater detail in aforenoted copending U.S. patent application Ser. No. 058109. In the present example, a fixed clock frequency of five megapixels per second is maintained.

AND 54 sets the memory location of the sweep number, diode number and magnitude of the event through the event counter 48 on bus 49 as an event ram address for the "Sweep Event" RAM 52, "Diode Event" RAM 51 and "Magnitude Event" RAM 53. It issues a "Save Signal" on lead 50 to each of RAMs 52, 51 and 53 so that the current sweep number on bus 47 is stored at its designated memory location in RAM 52, the current diode number from which the event signal was derived as present on bus 46 is stored at its designated memory location in RAM 51 and the vent magnitude is stored in RAM 53 at its designated memory location. "Save Signal" from AND 54 increments the event counter 48 after a delay sufficient to enable storage of the data in RAMs 52, 51 and 53 by passing that signal through delay 69 to the increment input 71 of counter 48.

The absolute magnitude of the event as received from the currently scanned diode of the camera at camera analog input 38 is passed by high pass filter 72 to analog to digital converter 73 from which it is passed in digital form for storage in "Magnitude Event" RAM 53.

Thus those events within the window defined between the limits set by "Begin Sweep" RAM 57 and "End Sweep" RAM 58 diode and sweep numbers which meet the threshold of magnitude defined for the diode and sweep number by "Threshold" RAM 67 are saved in "Sweep Event" RAM 52, "Diode Event" RAM 51 and "Magnitude Event" RAM 53 for processing by central processor 31.

Central processor 31 processes the data saved in the processor memory 75 after it has been transferred to that memory from "Sweep Event" RAM 52, "Diode Event" RAM 51, and "Magnitude Event" RAM 53. Control board 16 generates the signals to the cameras to acquire data, communicates with the servo controller to issue instructions such as "Center Cradle", "Cycle Cradle" or "Return to Home Position" and to pass saved data to the central processor. The executing program for the central processor board 31 issues commands to acquire data from the memories, analyzes the data and issues a decision about the inspected faceplate based on that analysis. It also communicates with the operating attendant through the video subsystem. At the end of an inspection routine analysis, the central processor issued a clear signal on lead 74 to the "Sweep Counter" 45 and the "Event Counter" 48 to reset those counters for the next inspection cycle.

Predetermined parameters are set in the system as through a keyboard at operator control 40. The begin sweep diode count for each sweep set in RAM 57 and end sweep diode count for each sweep set in RAM 58 can be set to define the window margins as to diode number and sweep number. "Threshold Select" RAM 66 provides a look up table to assign any of n threshold values for the diodes of a sweep as set by operator control. Thus the diode, pixel, or object area number along the band of a sweep, the sweep number, and the threshold signal magnitude can be predetermined selectively to define the inspection window and the threshold magnitude areas.

Inspection window limits for a line scan system can be set according to this invention employing various combinations of gating means to detect events either as dark areas in a light field or light areas in a dark field where the linear array of sensors can be exposed to a succession of bands of discrete areas on the successive objects to be inspected. The array can be moved relative to the objects, an optical element can be moved, or as illustrated, the objects can be moved relative to the array to expose the bands with the scan sweeps of the objects correlated with the exposed band of discrete means so that each discrete area is identified by its sensor number in the sweep and its sweep number. Signals from thus identified sensors can be utilized to identify areas from which characterizing signals are selectively gated as by AND gates 54 and 59 by control means responsive to the identification of the sensors, as by diode counter 43, and the identification of the scan sweep, as by sweep counter 45, for different longitudinal sensors for different individual scans both as to the sweep window limits and the threshold levels within those sweep windows. The window is defined at a beginning sensor, the count for which is set in RAM 57 or other suitable memory means to actuate comparator 55 on coincidence of a predetermined scan sweep and the scan of a predetermined sensor to enable gate 59, which enables gate 54. Similarly the sensor defining the end of the window for a sweep can be set in RAM 58 and actuate comparator 56 on coincidence of a predetermined scan sweep and the scan of a predetermined sensor to disable gate 59 and thus gate 54.

Threshold levels can be predetermined for each sensor along a scan individual to the sensors and to the scan sweeps according to the count in counters 43 and 45 by the "Threshold Select" RAM 66 which sets thresholds across the scan according to sweep number and applies those threshold individually to comparator 65 appropriate to the currently scanned sensor. Alternatively the "Threshold Select" RAM 66 could develop thresholds for given sensors for each scan and the "Threshold" RAM 67 could provide threshold signals to the comparator 64 for each sweep count as the coincidence of sensor count and sweep count occurs. Threshold signals cause comparator 64 to gate gate 54 within the window defined by gate 59.

These concepts can be employed in systems having different video signal sensing means from those disclosed. High pass filtered video can be viewed as spikes from a reference level occurring at the scan of pixels whose signal magnitude deviate from the video envelope and to a first order signal magnitudes deviating from the general reference level developed at the pixels free of defects and subject to the uniform light flux and the gradual deviations from uniformity of a non-defect type such as glass thickness changes. For example, windows of inspection and threshold magnitudes can be defined by diode count and sweep count in illumination invariant image processing systems as shown in U.S. Pat. Nos. 4,432,013, 4,437,116 and 4,467,350.

It is to be appreciated that the above disclosure is a preferred embodiment of the window and threshold definition by diode count and sweep count and that variations can be made employing the principles of this invention in other embodiments with other components without departing from its spirit or scope.

What is claimed is:

1. An apparatus for inspecting successive objects comprising:
   a linear array of sensors for providing a plurality of signals each representing the magnitude of light received from a corresponding discrete area along a band of discrete areas on an object;
   means to expose said linear array to a succession of bands of discrete areas on the object;
   means to can said linear array in a plurality of sweeps;
   means to identify and correlate each scan sweep with the exposure of a band of discrete areas on the object;
   means to identify individual sensors as they are subject to scan sweeps;
   signal utilization means for signals provided by said sensors;
   signal gating means for selectively passing sensor signals to said signal utilization means; and
   gate controlling means responsive to said means to identify sensors as predetermined individual sensors are identified and responsive to said means to identify scan sweeps as predetermined individual scan sweeps are identified to control said signal gating means for signals from different individual sensors during different individual scan sweeps.

2. An apparatus according to claim 1 wherein said gate controlling means comprises a signal comparator which issues controlling signal upon a coincidence of a predetermined scan sweep and the scan of a predetermined sensor.

3. An apparatus according to claim 2 including memory means which issues a scan sweep identification signal for individual scans as individual sensors are scanned, and wherein said comparator issues a controlling signal in response to a coincidence of a scan sweep identification for a given sweep from said memory means and a scan sweep identification for said given sweep from means to identify scan sweeps.

4. An apparatus according to claim 1 wherein said means to identify each scan sweep is a scan sweep counter.

5. An apparatus according to claim 1 wherein said means to identify individual sensors is a sensor counter.

6. An apparatus according to claim 1 wherein said gate controlling means enables said gate.

7. An apparatus according to claim 1 wherein said gate controlling means disables said gate.

8. An apparatus according to claim 6 wherein said gate controlling means includes means to disable said gate for signals from different individual sensors during different individual scan sweeps which follow enable signals for said scan sweeps and wherein said gating means is maintained enabled during a scan sweep following response of said gate enabling until response during said scan sweep of said gate disabling means.

9. An apparatus according to claim 8 wherein said gate enabling means comprises a signal comparator which issues an enabling signal upon a coincidence of a predetermined scan sweep and the scan of a first predetermined sensor, and wherein said gate disabling means comprises a signal comparator which issues a disabling signal upon a coincidence of said predetermined scan sweep and the scan of a second predetermined sensor.

10. An apparatus according to claim 1 including a signal threshold defining means for defining a plurality of individual different threshold signal levels for signals from at least some of said individual sensors;

said gate controlling means including means responsive to individual sensor signal which have a predetermined relationship to threshold signal levels for said individual sensor set by said signal threshold defining means.

11. An apparatus according to claim 10 wherein said gate controlling means enabling said gate in response to said individual sensor signal levels of at least the threshold signal levels.

12. An apparatus according to claim 10 wherein said means for defining threshold signal levels for signals from individual sensors defines different threshold levels for at least some of said individual sensors during different predetermined scan sweeps of said sensors.

13. An apparatus according to claim 10 wherein said signal threshold defining means comprises a threshold memory containing look-up tables for individual threshold signal levels of each of a plurality of sensors for each of a plurality of individual scan sweeps responsive to the means to identify individual scan sweeps to set a threshold signal level individual to said sensor and said scan sweep; and including a comparator to issue a signal to said gate controlling means in response to a predetermined relationship between a signal from one of said sensors and the set threshold signal level individual to said sensor and said scan sweep.

14. An apparatus according to claim 12 wherein said gate controlling means includes means for enabling said gate and means for disabling said gate and wherein said means for enabling and means for disabling are independent of said means responsive to individual sensor signals which have a predetermined relationship to threshold signal levels.

15. An apparatus for detecting defects in successive objects including a linear array of sensors for providing a plurality of signals each representing the magnitude of light received from a corresponding discrete area along a band of discrete areas on an object; means to move said linear array and object relative to each other to expose said linear array to a succession of bands of discrete areas on the object; means to scan said linear array in a plurality of sweeps correlated with exposure to the bands of discrete areas on the object; means to identify the sweep number and sensor number for each discrete area as it is scanned; means for generating for each one of said sensors for each sweep a signal which is a function of the magnitude of light received by said sensor from its corresponding discrete area to which it is exposed; means for storing a plurality of individual threshold signals for each of a plurality of sensors of said linear array; means for activating an individual stored threshold signal for each of said plurality of sensors in response to the sweep number and the sensor number from said means to identify; and means for comparing said generated signal for a discrete area with the activated threshold signal in said means for storing for the corresponding sensor number and sweep number for said area and issuing an event signal when the magnitude of said generated signal is at least the magnitude of said corresponding activated threshold signal.

16. An apparatus according to claim 15 including means to enable said means issuing an event signal for each sweep of said linear array between sensor limits along said linear array which is predetermined individually for each sweep.

17. An apparatus according to claim 15 including a sweep counter to count the sweeps of each object, a sensor counter to count the sensors as scanned in each sweep; a threshold select memory responsive to the sweep count of said sweep counter to establish threshold signal magnitudes for each sensor for said sweep count; a threshold memory for issuing a threshold signal magnitude to said means for comparing in response to the established threshold of said threshold select memory for the sweep count and the sensor count of said sensor counter.

18. An apparatus according to claim 15 including means to enable the issuance of an event signal; first means to define an individual sensor for each of a plurality of bands of discrete areas at which said means to enable is activated; and second means to define an individual sensor for each of a plurality of bands of discrete areas at which said means to enable is disabled.

19. An apparatus according to claim 18 wherein said first means for each band of discrete areas precedes said second means in the sequence of a sweep of sensors.

20. An apparatus according to claim 18 including a sensor counter to count the sensors scanned; a sweep counter to count the number of scans of the bands of discrete areas; said first means including a begin sweep memory for storing a sensor count at which to begin response to sensed signal magnitudes at individual discrete areas for each of a plurality of bands defined by said sweep counter and to activate said means to enable; said second means including an end sweep memory for storing a sensor count at which to terminate response to sensed signal magnitudes at individual discrete areas for each of a plurality of bands defined by said sweep counter.

21. Apparatus for detecting defects in successive objects including a linear array of sensors for providing a plurality of signals each representing the magnitude of light received from a corresponding discrete area along a band of discrete areas on the object; means to move said linear array and object relative to each other to expose said linear array to a succession of bands of discrete areas on the object; means to scan said linear array with a plurality of sweeps; means responsive to signals from scanned sensors; and means to enable said means responsive to signals for each sweep of said linear array between sensor limits along said linear array which are predetermined individually for each sweep.

22. An apparatus according to claim 21 wherein said means to enable includes a sensor counter for counting scanned sensors in each sweep; a sweep counter; a begin sweep memory issuing a sweep count in response to sensor count at which such sweep is to become effective; a begin sweep comparator issuing an enable signal to said means to enable when said sweep count from said begin sweep memory matches said sweep count from said sweep counter; an end sweep memory issuing a sweep count in response to a sensor count at which such sweep is to be disabled; and an end sweep comparator issuing a disable signal to said means to enable when said sweep count from said end sweep memory matches said sweep count from said sweep counter.

23. An apparatus according to claim 22 wherein said means to enable includes a coincidence gate to issue an enable signal in response to a coincidence of enable signals from said begin sweep comparator and said end sweep comparator.

24. An apparatus according to claim 15 wherein said means for comparing includes a threshold comparator; means to apply signals which are a function of scanned sensor signals to said comparator; and means to apply threshold signals from said threshold memory to said threshold comparator; said threshold comparator issuing said event signal when said signal which is a function of said scanned sensor signal is at least said threshold signal level.

25. The method of detecting defects in successive objects comprising sequentially sensing the magnitude of light received from a plurality of adjacent bands of aligned discrete areas swept in successive bands displaced from each other on the object; generating a signal which is a function of the sensed magnitude of light from each of a plurality of the discrete areas; identifying the discrete areas for which the signal is generated by band in which such area lies and its position along such band; storing a plurality of individual threshold signal magnitudes, one for each discrete area designated by the band in which such area lies and the position along such band of such area; activating an individual stored threshold signal for each identified discrete area while a signal is generated for such area by designating the stored threshold signal by the band in which such area lies and the position along such band of such area; comparing the generated signal magnitude for a discrete area with the activated threshold signal magnitude for such area; and issuing an event signal when the magnitude of the generated signal has a predetermined relationship to the magnitude of the activated threshold signal.

26. The method according to claim 25 including inhibiting the issuing of event signals for each of a plurality of sweep bands for a plurality of discrete areas comprising portions of each of those bands and enabling the issuing of event signals for each of such plurality of swept bands for a plurality of discrete areas comprising portions of each of those bands.

27. The method according to claim 25 including the steps of counting each discrete area in a band; counting each sweep band; selectively inhibiting the issuing of an event signal during first predetermined discrete area counts during predetermined swept band counts; and selectively enabling the issuing of event signals during second predetermined discrete area counts during such predetermined swept band counts.

28. The method according to claim 25 including the steps of counting each discrete area in a band; counting each swept band; selectively activating threshold signal magnitudes for each of a plurality of discrete areas in individual bands in response to each of a plurality of swept band counts; and selectively activating a threshold signal magnitude for each of a plurality of discrete areas in a selectively activated band in response to each of a plurality of discrete area counts.

29. The method of detecting defects in successive objects comprising sequentially sensing the magnitude of light received from a series of aligned discrete areas swept in successive bands displaced from each other on the object; generating a signal which is a function of the difference in sensed magnitude of light from each of a plurality of the discrete areas from the magnitude of light from preceding discrete areas; comparing the difference signal for a discrete area with a threshold signal magnitude; issuing an event signal when the magnitude of the difference signal differs from the magnitude of the compared threshold signal; counting each discrete area in a band as it is swept; counting each swept band; selectively inhibiting the issuing of an event signal during first predetermined discrete area counts individual to predetermined swept band counts; and selectively enabling the issuing of an event signal during second predetermined discrete area counts other than said first predetermined discrete area counts during such predetermined swept band counts.

* * * * *